US012617727B2

(12) United States Patent
Matsuura et al.

(10) Patent No.: US 12,617,727 B2
(45) Date of Patent: May 5, 2026

(54) METHOD FOR PRODUCING ZIRCONIA SINTERED BODY

(71) Applicant: KURARAY NORITAKE DENTAL INC., Kurashiki (JP)

(72) Inventors: Atsushi Matsuura, Aichi (JP); Hiroyuki Sakamoto, Aichi (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 990 days.

(21) Appl. No.: 17/787,521

(22) PCT Filed: Dec. 18, 2020

(86) PCT No.: PCT/JP2020/047570
§ 371 (c)(1),
(2) Date: Jun. 20, 2022

(87) PCT Pub. No.: WO2021/125351
PCT Pub. Date: Jun. 24, 2021

(65) Prior Publication Data
US 2022/0380259 A1 Dec. 1, 2022

(30) Foreign Application Priority Data

Dec. 20, 2019 (JP) ................................. 2019-229979

(51) Int. Cl.
*C04B 35/64* (2006.01)
*A61K 6/818* (2020.01)
*C04B 35/48* (2006.01)

(52) U.S. Cl.
CPC .............. *C04B 35/48* (2013.01); *A61K 6/818* (2020.01); *C04B 35/64* (2013.01);
(Continued)

(58) Field of Classification Search
CPC ....... C04B 35/48; C04B 35/64; C04B 35/486; C04B 2235/656; C04B 2235/3224;
(Continued)

(56) References Cited

U.S. PATENT DOCUMENTS

| | | | |
|---|---|---|---|
| 2010/0248936 A1 | 9/2010 | Yamada et al. | |
| 2011/0027742 A1 | 2/2011 | Fujisaki et al. | |
| 2015/0247672 A1 | 9/2015 | Schmidt et al. | |

FOREIGN PATENT DOCUMENTS

| | | |
|---|---|---|
| CN | 107162603 A | 9/2017 |
| EP | 3 511 137 A1 | 7/2019 |

(Continued)

OTHER PUBLICATIONS

JP2016060687A_Description_20250609_122.pdf, JP2016060687A, English translation Description, Yoshida et. al., "method for producing translucent zirconia sintered compact, translucent zirconia sintered compact , etc . . . ", Escpacenet, Jun. 9, 2025 (Year: 2016).*

(Continued)

*Primary Examiner* — Alison L Hindenlang
*Assistant Examiner* — Christopher Paul Daigler
(74) *Attorney, Agent, or Firm* — Oblon, McClelland, Maier & Neustadt, L.L.P.

(57) ABSTRACT

A method for producing a zirconia sintered body includes: heating a zirconia molded body or a zirconia pre-sintered body, the heating includes a temperature increasing step, and a rate of temperature increase in a temperature region from a temperature at which the zirconia starts to shrink to a temperature at which the zirconia finishes shrinking in the temperature increasing step is adjusted to enable the zirconia molded body or the zirconia pre-sintered body to shrink at substantially a constant rate during temperature increase in (Continued)

each of zones of when the temperature region is evenly divided into a plurality of zones of specific temperature ranges.

6 Claims, 3 Drawing Sheets

(52) U.S. Cl.
CPC    *C04B 2235/3244* (2013.01); *C04B 2235/656* (2013.01); *C04B 2235/9615* (2013.01)

(58) Field of Classification Search
CPC . C04B 2235/9615; A61C 13/00; A61C 13/08; A61C 13/087; A61C 5/70; A61C 8/00; A61K 6/818
See application file for complete search history.

(56) References Cited

FOREIGN PATENT DOCUMENTS

| | | | |
|---|---|---|---|
| JP | 2-255573 | A | 10/1990 |
| JP | 4-50171 | A | 2/1992 |
| JP | 4-1 43646 | A | 5/1992 |
| JP | 10-78400 | A | 3/1998 |
| JP | 2010-220779 | A | 10/2010 |
| JP | 2015-531048 | A | 10/2015 |
| JP | 2016-60687 | A | 4/2016 |
| JP | 2016-527017 | A | 9/2016 |
| WO | WO 2015/011079 | A1 | 1/2015 |

OTHER PUBLICATIONS

JPH04143646A_Description_20250609_1337.pdf, JPH04143646A, English translation Description, Abe et, al., "method for controlling sintering of material", Espacenent, Jun. 9, 2025 (Year: 1992).*

CN107162603A_Claims_20250609_1525.pdf, CN107162603A, English translation Claims, Li et, al. "Rapid sintering method for a dental zirconium oxide ceramic", Espacenet, Jun. 9, 2025 (Year: 2017).*

Extended European Search Report issued Dec. 20, 2023 in European Patent Application No. 20903493.3, 9 pages.

International Search Report issued Feb. 9, 2021 in PCT/JP2020/047570 filed Dec. 18, 2020, 3 pages.

\* cited by examiner

| Sample Name | Firing Conditions | Model Conformity | Image | Distance Between Marginal Portions |
|---|---|---|---|---|
| Example 1 | Table 1 | Good | | 0.01 mm |
| Comparative Example 1 | Table 7 | Poor | | 0.94 mm |
| Example 2 | Table 3 | Good | | 0.16 mm |
| Comparative Example 2 | Table 7 | Poor | | 1.21 mm |
| Example 3 | Table 5 | Good | | 0.12 mm |
| Comparative Example 3 | Table 8 | Poor | | 1.65 mm |

METHOD FOR PRODUCING ZIRCONIA SINTERED BODY

TECHNICAL FIELD

The present invention relates to a method for producing a zirconia sintered body.

BACKGROUND ART

For years, metal has been used for a range of dental products, including, for example, prostheses (such as veneer crowns, dental caps, crowns, and post crowns), orthodontic products, and products for dental implants. However, metals lack aesthetic quality because of the colors that are distinctively different from the color of natural teeth, and can cause allergic reaction when released from these products. These issues involving the use of metal have been addressed by dental products that use ceramic materials such as aluminum oxide (alumina) and zirconium oxide (zirconia) as alternative materials of metal. Particularly, zirconia excels in strength, and has relatively good aesthetics, and this, combined with the currently declining price of zirconia, has created a high demand for this material.

In fabrication of a dental prosthesis with zirconia, a block unit or a disc-shaped work for milling (a material to be milled) that has been pre-sintered at a temperature about 400° C. to 700° C. below the temperature that produces an ideal sintered body is cut into a shape of a dental prosthesis with CAD/CAM equipment. The resulting workpiece of unsintered zirconia is then sintered by being held at a temperature as high as 1,400° C. to 1,650° C. The whole process from the start of temperature increase to the end of temperature decrease typically takes a total of 6 to 12 hours, including the retention period between temperature increase and temperature decrease. In response to a growing demand for short firing at the dental clinic, a furnace is proposed that enables firing in a short time period, as described in Patent Literature 1. However, such short firing involves deformation or distortion in fabrication of a large-sized prosthesis.

Patent Literature 2, which relates to multilayer oxide ceramic bodies, particularly pre-sintered multilayer oxide ceramic blanks and oxide ceramic green bodies suited for dental applications, describes a pre-sintered multilayer oxide ceramic blank having a distortion coefficient (d=(HV$_{max}$−HV$_{MIN}$)/HV$_{AVE}$) of less than 0.4. While this enables reduction of prosthesis deformation, the technique is limited to a certain composition, and, even with this composition, involves deformation in large-sized prostheses (about twice as large as the 3 to 4 cm length described in Examples).

CITATION LIST

Patent Literature

Patent Literature 1: JP 2015-531048 T
Patent Literature 2: JP 2016-527017 T

SUMMARY OF INVENTION

Technical Problem

It is accordingly an object of the present invention to provide a method of production of a zirconia sintered body that enables firing in a short time period, and that can reduce deformation even in large-sized prostheses, without limiting the composition.

Solution to Problem

The present inventors conducted intensive studies to find a solution to the foregoing problems, and found that the above issues can be solved with a short firing schedule created by adjusting the rate of temperature increase to specific rates. The present invention was completed after further studies based on this finding.

Specifically, the present invention includes the following.

[1] A method for producing a zirconia sintered body, comprising a heating step of heating a zirconia molded body or a zirconia pre-sintered body, wherein:

the heating step includes a temperature increasing step, and a rate of temperature increase in a temperature region from a temperature at which the zirconia starts to shrink to a temperature at which the zirconia finishes shrinking in the temperature increasing step is adjusted to enable the zirconia molded body or the zirconia pre-sintered body to shrink at substantially a constant rate during temperature increase in each of zones of when the temperature region is evenly divided into a plurality of zones of specific temperature ranges.

[2] The method according to [1], wherein the temperature range of each zone is 50° C.

[3] The method according to [1] or [2], wherein the rate of temperature increase in each zone is set to be 0.1 to 1.0 times an acceptable rate of temperature increase in each zone calculated from the formula (1) below, and a ratio of the rate of temperature increase in each zone to the acceptable rate of temperature increase in each zone is substantially the same, $$
\begin{aligned}
&\text{(Acceptable rate of temperature increase in each} \\
&\quad \text{zone)=(maximum rate of temperature increase} \\
&\quad \text{of furnace)/(coefficient of shrinkage of each} \\
&\quad \text{zone)} \qquad\qquad\qquad\qquad\qquad\qquad (1),
\end{aligned}
$$

wherein the coefficient of shrinkage of each zone in formula (1) is represented by the following formula (2), $$
\begin{aligned}
&\text{(Coefficient of shrinkage of each zone)=(shrinkage} \\
&\quad \text{rate difference of each zone)/(temperature} \\
&\quad \text{range/100)} \qquad\qquad\qquad\qquad\qquad (2),
\end{aligned}
$$

wherein the formula (1) is solved by assuming that the coefficient of shrinkage of each zone is 1 when the coefficient of shrinkage of each zone calculated using formula (2) is less than 1.

[4] The method according to any one of [1] to [3], wherein the temperature region ranges from 1,050 to 1,400° C.

[5] The method according to any one of [1] to [4], which has a total firing time of at most 120 minutes from a start of temperature increase in the temperature increasing step to an end of a retention period at the highest firing temperature of the temperature increasing step.

[6] The method according to any one of [1] to [5], wherein the heating step further includes a retention step of retaining the highest firing temperature of the temperature increasing step, following the temperature increasing step.

[7] The method according to any one of [1] to [6], wherein the zirconia sintered body is for dental use.

Advantageous Effects of Invention

According to the present invention, a method of production of a zirconia sintered body can be provided that enables firing in a short time period, and that can reduce deformation even in large-sized prostheses, without limiting the composition. In this way, the time needed by a user (at the dental laboratory or dental clinic) to repair deformation can be eliminated to reduce the overall time of a user fabricating a prosthesis. A method of production of a zirconia sintered body of the present invention can produce a zirconia sintered body having high model conformity.

DESCRIPTION OF EMBODIMENTS

Figure 1A:
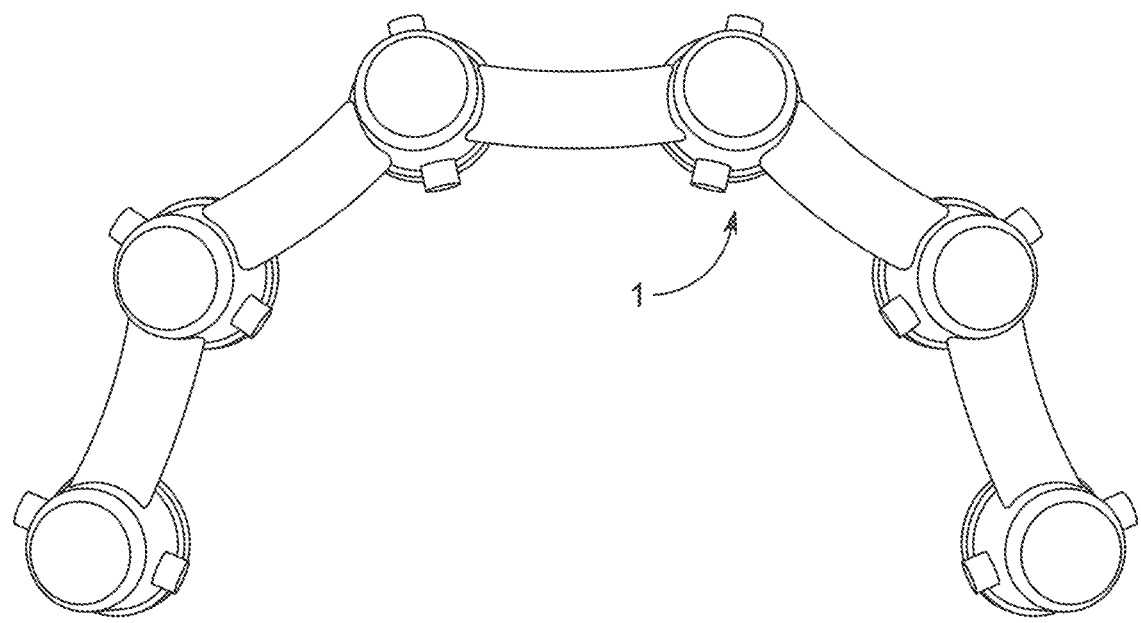
FIG. 1 is a diagram showing the shape of prostheses produced in Examples 1 to 3 and Comparative Examples 1 to 3.

Importantly, a method for producing a zirconia sintered body of the present invention comprises a heating step of heating a zirconia molded body or a zirconia pre-sintered body, wherein: the heating step includes a temperature increasing step, and a rate of temperature increase in a temperature region from a temperature at which the zirconia starts to shrink to a temperature at which the zirconia finishes shrinking in the temperature increasing step is adjusted to enable the zirconia molded body or the zirconia pre-sintered body to shrink at substantially a constant rate during temperature increase in each of zones of when the temperature region is evenly divided into a plurality of zones of specific temperature ranges. The present invention is described below in detail.

In the present invention, the temperature increasing step heats a zirconia molded body or a zirconia pre-sintered body with a furnace that has been heated to, for example, at least room temperature, or to a temperature higher than room temperature and no higher than 500° C. Preferably, the zirconia molded body or zirconia pre-sintered body subjected to firing is one having a predetermined shape of a dental product. Examples of the dental product include dental prostheses (such as veneer crowns, dental caps, crowns, and post crowns), orthodontic products, and products for dental implants. The zirconia molded body or zirconia pre-sintered body to be heated may be one that has been processed with dental CAD/CAM equipment, or one fabricated by a denturist using a process such as milling.

For firing, a zirconia molded body or a zirconia pre-sintered body to be heated may be directly placed on a muffle member of a furnace, or may be placed in a furnace using a tray, a pedestal, or a pin made of ceramic or high-melting-point metal. Alternatively, ceramic beads may be used to place a zirconia molded body or a zirconia pre-sintered body.

The start temperature of the temperature increasing step is room temperature to 500° C., preferably room temperature to 400° C., more preferably room temperature to 300° C., even more preferably room temperature to 200° C. The rate of temperature increase before the temperature increasing step is started is not particularly limited, as long as the temperature increasing step starts with these start temperatures.

The furnace used for firing in the present invention is an atmospheric furnace. The furnace may be a box furnace, a crucible furnace, a tube furnace, an elevator furnace, a continuous furnace, or a rotary kiln, or may be a resistance heating furnace, an induction heating furnace, a directcurrent electric furnace, an IH furnace, a high-frequency furnace, or a microwave furnace. Alternatively, for example, a metallic heating element, silicon carbide, molybdenum disilicide, lanthanum chromite, molybdenum, carbon, or tungsten may be used as a heating element, and SiC may be used as a susceptor. The furnace may be a combination of two or more of these furnaces. Heat efficiency improves, and the heat in the furnace can be more easily maintained during firing when the furnace has a smaller volume in the chamber where a pedestal for placing a zirconia molded body or a zirconia pre-sintered body of a predetermined shape such as a dental cap is placed.

In the present invention, the following methods can be used to determine the temperature region (hereinafter, also referred to as "shrinkage temperature region"), which is a range of temperature from a temperature at which the zirconia starts to shrink (hereinafter, also referred to as "shrinkage start temperature") to a temperature at which the zirconia finishes shrinking (hereinafter, also referred to as "shrinkage end temperature"). Here, "shrinkage start temperature" indicates the lowest firing temperature at which a prepared cuboidal sample block of unfired zirconia (1 cm×2 cm×1 cm) has a shrinkage rate of more than 0% when the sample block is fired with the furnace for a specific time period (for example, 10 minutes) at a firing temperature higher than the start temperature of the temperature increasing step. The method of measurement of shrinkage rate will be described later. Shrinkage end temperature indicates the lowest temperature at which the difference between the shrinkage rate (%) at a firing temperature T (° C.) and the shrinkage rate (%) at a firing temperature T+50° C. is 0%, for example, when the temperature range of each zone of the shrinkage temperature region is 50° C. The temperature region may be, for example, 1,000 to 1,600° C., 1,000 to 1,500° C., or 1,050 to 1,400° C., though it depends on factors such as the content of a stabilizer (described later).

In the present invention, the shrinkage rate at a specific firing temperature can be determined as follows. A prepared cuboidal sample block of unfired zirconia (1 cm×2 cm×1 cm) is fired at a specific firing temperature, and the length of the fired sample block is measured along the x-axis (n=3). The shrinkage rate (%) along x-axis is then calculated from the formula below, and the mean value is calculated as the shrinkage rate along x-axis.

$$\text{(Shrinkage rate (\%) along } x\text{-axis)} = [(\text{length along } x\text{-axis before firing}) - (\text{length along } x\text{-axis after firing})] \times 100/(\text{length along } x\text{-axis before firing})$$

In the same fashion, shrinkage rate is also calculated for the y-axis and z-axis, and the mean value of the three shrinkage rates is calculated as the shrinkage rate (%) at the temperature of firing.

In the present invention, the method of adjusting the rate of temperature increase is not particularly limited, as long as the zirconia molded body or zirconia pre-sintered body shrinks at substantially a constant rate in each temperature zone during temperature increase. However, as a specific example of a preferred embodiment, the rate of temperature increase of each zone can be determined using a method including the following steps 1 to 5.

Step 1

A region of temperature from shrinkage start temperature to shrinkage end temperature is evenly divided into a plurality of zones of specific temperature ranges, and the shrinkage rates in response to firing at the firing temperatures at the boundaries of each zone (temperature range) are measured. Here, the retention time (holding time) at each temperature is constant.

Step 2

From the shrinkage rates measured in Step 1 at the firing temperatures at the boundaries of each zone, the difference of shrinkage rates at the start temperature and end temperature of each zone is calculated as a shrinkage rate difference of each zone.

Step 3

A coefficient of shrinkage in each zone is calculated using the following formula.

(Coefficient of shrinkage of each zone)=(shrinkage rate difference of each zone)/(temperature range/100)      (2)

The coefficient of shrinkage of each zone is assumed to be 1 when the coefficient of shrinkage of each zone calculated using formula (2) is less than 1.

Step 4

An acceptable rate of temperature increase in each zone is calculated using the following formula.

(Acceptable rate of temperature increase in each zone)=(maximum rate of temperature increase of furnace)/(coefficient of shrinkage of each zone)      (1)

Step 5

The rate of temperature increase in each zone is set to be 0.1 to 1.0 times the acceptable rate of temperature increase in each zone. The ratio of the rate of temperature increase in each zone to the acceptable rate of temperature increase in each zone is substantially the same.

Preferably, Step 1 is preceded by a step of determining a temperature region between shrinkage start temperature and shrinkage end temperature. The temperature region can be determined from the shrinkage start temperature and shrinkage end temperature measured by measuring the shrinkage rates of a predetermined sample block of unfired zirconia by firing the sample block with a furnace using the method described above.

In Step 1, the specific zones (temperature ranges) of equal intervals can be set as appropriate according to the desired accuracy with which deformation should be reduced. For example, the temperature range may be 100° C., and is preferably 50° C., even more preferably 20° C. The number of zones of equal intervals can be set as appropriate according to the desired accuracy with which deformation should be reduced. For example, the number of zones may be 4 or more, or 5 or more.

In Step 3, the coefficient of shrinkage in each zone is assumed to be 1 when the coefficient of shrinkage of each zone calculated using formula (2) is less than 1. This is needed for determination of an appropriate acceptable rate of temperature increase needed for the shrinkage of a zirconia molded body or a zirconia pre-sintered body to take place at substantially a constant rate during temperature increase in each zone of the shrinkage temperature region in the temperature increasing step, and thereby reduce deformation due to shrinkage. In formula (2), "temperature range" is substituted for "50" when the temperature range is, for example, 50° C., and "shrinkage rate difference of each zone" is substituted for "1.5" when the shrinkage rate difference in a given zone is 1.5%.

The acceptable rate of temperature increase of each zone calculated in Step 4 is a value indicated by formula (1), and serves as a reference of the acceptable rate of temperature increase needed for the shrinkage of a zirconia molded body or a zirconia pre-sintered body to take place at substantially a constant rate during temperature increase in each zone of the shrinkage temperature region in the temperature increasing step, and thereby reduce deformation due to shrinkage. The maximum rate of temperature increase of furnace is not particularly limited, as long as it falls within a range allowable by the capabilities of the furnace. For example, the maximum rate of temperature increase of furnace may have any value appropriately set within a range of from about 30° C./min to 200° C./min, or about 50° C./min to 120° C./min.

It may not be possible to sufficiently reduce deformation when the rate of temperature increase in each zone is more than 1.0 times the acceptable rate of temperature increase in each zone in Step 5. It may not be possible to perform short firing when the rate of temperature increase in each zone is less than 0.1 times the acceptable rate of temperature increase in each zone in Step 5. In view of enabling shorter firing while reducing deformation, the rate of temperature increase in each zone set in Step 5 is preferably 0.2 to 1.0 times, more preferably 0.5 to 1.0 times, even more preferably 0.8 to 1.0 times the acceptable rate of temperature increase in each zone. In order for the shrinkage of a zirconia molded body or a zirconia pre-sintered body to take place at substantially a constant rate during temperature increase in each zone, it is preferable that the ratio of rate of temperature increase to acceptable rate of temperature increase be set to a predetermined uniform value in all zones (for example, the rate of temperature increase is 1.0 times the acceptable rate of temperature increase in all zones). In other words, it is preferable that the ratio of the rate of temperature increase in each zone to the acceptable rate of temperature increase in each zone be substantially the same. Here, "substantially the same" means that the ratio of rate of temperature increase to acceptable rate of temperature increase in a given zone differs from the ratio of rate of temperature increase to acceptable rate of temperature increase in a different zone by preferably less than 10%, more preferably at most 6%, even more preferably at most 5%. In view of controlling the shrinkage rate of a zirconia molded body or a zirconia pre-sintered body during temperature increase in each zone, it is more preferable to set the same value for the ratio of rate of temperature increase to acceptable rate of temperature increase in each zone.

By determining and adjusting the rate of temperature increase in each zone using the foregoing method including Steps 1 to 5, a more gradual rate of temperature increase can be provided in temperature zones involving large shrinkage, and a faster rate of temperature increase can be provided in temperature zones in which the extent of shrinkage is smaller. In this way, a zirconia molded body or a zirconia pre-sintered body can shrink at substantially a constant rate during temperature increase in each zone of the temperature region between shrinkage start temperature and shrinkage end temperature. This solves the uneven heating that occurs when a large-sized prosthesis (a large dental prosthesis with three or more bridge units, such as a long-span bridge) is fired. Accordingly, shrinkage occurs in a uniform fashion throughout the prosthesis being fired. In the present invention, the shrinkage rate of each zone during temperature increase can be calculated using the following formula.

(Shrinkage rate of each zone during temperature increase)={(dimensions at the start temperature of the zone)−(dimensions at the end temperature of the zone)}/(dimensions at the start temperature of the zone)

This formula is used to calculate shrinkage rates during temperature increase as measures of dimensional changes along the x-, y-, and z-axes, and the mean value of shrinkage rates along these axes is calculated as the shrinkage rate during temperature increase in the zone of interest. Here, "substantially constant" used in conjunction with a shrinkage rate of a zirconia molded body or a zirconia pre-sintered body during temperature increase in each zone indicates that the shrinkage rate during temperature increase calculated for each zone is 0.8 to 1.2 times its mean value.

In the present invention, the rate of temperature increase in the temperature increasing step before shrinkage start temperature is, for example, 50° C./min or more. In view of reduction of a processing time, the rate of temperature increase in the temperature increasing step before shrinkage start temperature is preferably 60° C./min or more, more preferably 70° C./min or more, even more preferably 80° C./min or more. The rate of temperature increase in the temperature increasing step before shrinkage start temperature is 500° C./min or less, preferably 450° C./min or less, more preferably 400° C./min or less, even more preferably 350° C./min or less. When the rate of temperature increase in the temperature increasing step before shrinkage start temperature is more than 500° C./min, fractures or cracks may occur during firing. When water used for processing or a staining color liquid is present in the zirconia molded body or zirconia pre-sintered body, the temperature increasing step may be started after drying for 1 to 20 minutes, preferably 5 to 15 minutes, at 300° C. or less.

The zirconia molded body or zirconia pre-sintered body used for a method of production of a zirconia sintered body of the present invention is preferably one that contains, in addition to zirconia, a stabilizer capable of reducing phase transformation of zirconia. Such a zirconia molded body or zirconia pre-sintered body is preferably a zirconia molded body or zirconia pre-sintered body in which at least a part of the stabilizer is not dissolved in zirconia in the form of a solid solution. The stabilizer is preferably one capable of forming partially stabilized zirconia.

Examples of the stabilizer include calcium oxide (CaO), magnesium oxide (MgO), yttria, cerium oxide ($CeO_2$), scandium oxide ($Sc_2O_3$), niobium oxide ($Nb_2O_5$), lanthanum oxide ($La_2O_3$), erbium oxide ($Er_2O_3$), praseodymium oxide ($Pr_6O_{11}$), samarium oxide ($Sm_2O_3$), europium oxide ($Eu_2O_3$), and thulium oxide ($Tm_2O_3$). The stabilizer may be used alone, or two or more thereof may be used in combination. The stabilizer content in a zirconia pre-sintered body and a sintered body thereof of the present invention can be measured, for example, by inductively coupled plasma (ICP) emission spectral analysis or x-ray fluorescence analysis. The stabilizer content in a zirconia pre-sintered body or a sintered body thereof of the present invention is preferably 0.1 to 18 mol %, more preferably 1 to 15 mol %, even more preferably 2 to 8 mol % relative to the total number of moles of zirconia and stabilizer. In view of the strength and translucency of the zirconia sintered body obtained, the zirconia molded body or zirconia pre-sintered body preferably contains yttria as a stabilizer. The yttria content is preferably 3.0 mol % or more, more preferably 3.5 mol % or more, even more preferably 3.8 mol % or more, particularly preferably 4.0 mol % or more relative to the total number of moles of zirconia and yttria. The zirconia sintered body can have improved translucency with a yttria content of 3.0 mol % or more. The yttria content is preferably 7.5 mol % or less, more preferably 7.0 mol % or less, even more preferably 6.5 mol % or less, particularly preferably 6.0 mol % or less relative to the total number of moles of zirconia and yttria. A decrease in the strength of the zirconia sintered body can be reduced with a yttria content of 7.5 mol % or less.

In a zirconia molded body or a zirconia pre-sintered body of the present invention, it is preferable that at least a part of the stabilizer be not dissolved in zirconia in the form of a solid solution. A part of stabilizer not being dissolved in zirconia in the form of a solid solution can be confirmed, for example, by XRD patterns. A stabilizer not dissolved in zirconia in the form of a solid solution is present in the zirconia molded body or zirconia pre-sintered body when a peak attributed to the stabilizer is confirmed in an XRD pattern of the zirconia pre-sintered body. Basically, an XRD pattern does not show a peak attributed to the stabilizer when the stabilizer is fully dissolved in the form of a solid solution. However, depending on conditions such as the crystal state of the stabilizer, the absence of a stabilizer peak in an XRD pattern does not necessarily mean that the stabilizer is dissolved in zirconia in the form of a solid solution. The stabilizer can be thought as having almost fully or basically fully dissolved in zirconia in the form of a solid solution when the main crystal system of zirconia is a tetragonal and/or cubic crystal system and when the XRD pattern does not show a peak attributed to the stabilizer. In a zirconia molded body or a zirconia pre-sintered body of the present invention, it is not necessarily required that the stabilizer be fully dissolved in zirconia in the form of a solid solution. As used herein, "stabilizer being dissolved in the form of a solid solution" means that, for example, elements (atoms) present in the stabilizer are dissolved in zirconia in the form of a solid solution.

In a zirconia molded body or a zirconia pre-sintered body of the present invention, the percentage presence $f_y$ of yttria not dissolved in zirconia in the form of a solid solution (hereinafter, also referred to as "undissolved yttria") can be calculated using the formula (3) below. The percentage presence $f_y$ of undissolved yttria is preferably greater than 0%, more preferably 1% or greater, even more preferably 2% or greater, particularly preferably 3% or greater. The percentage presence $f_y$ of undissolved yttria may be, for example, at most 15%. Preferably, the upper limit of the percentage presence $f_y$ of undissolved yttria is dependent on the content of yttria in the zirconia molded body or zirconia pre-sintered body. The percentage presence $f_y$ may be at most 7% when the yttria content is 3 mol % or more and less than 4.5 mol %. The percentage presence $f_y$ may be at most 11% when the yttria content is 4.5 mol % or more and less than 5.8 mol %. The percentage presence $f_y$ may be at most 15% when the yttria content is 5.8 mol % to 7.5 mol %.

In a zirconia molded body or a zirconia pre-sintered body of the present invention, the percentage presence $f_y$ is preferably 0.5% or greater, more preferably 1.0% or greater, even more preferably 2.0% or greater when the yttria content is 3 mol % or more and less than 4.5 mol %. The percentage presence $f_y$ is preferably 1% or greater, more preferably 2% or greater, even more preferably 3% or greater when the yttria content is 4.5 mol % or more and less than 5.8 mol %. The percentage presence $f_y$ is preferably 2% or greater, more preferably 3% or greater, even more preferably 4% or greater when the yttria content is 5.8 mol % to 7.5 mol %.

[Math. 1]

$$f_y(\%) = \frac{I_y(111)}{I_y(111) + I_m(111) + I_m(11-1) + I_t(111) + I_c(111)} \times 100 \quad (3)$$

In formula (3), $I_y(111)$ represents the peak intensity of the (111) plane of yttria near $2\theta=29°$ in an XRD pattern by CuKα radiation, $I_m(111)$ and $I_m(11-1)$ represent the peak intensities of the (111) plane and (11-1) plane, respectively, of the monoclinic system of zirconia, $I_t(111)$ represents the peak intensity of the tetragonal (111) plane of zirconia, and $I_c(111)$ represents the peak intensity of the (111) plane of the cubic crystal system of zirconia.

By substituting $I_y(111)$ for other peaks, the formula (3) can be used to calculate the percentage presence of an undissolved fraction of a stabilizer other than yttria.

Preferably, the crystal system of zirconia in a zirconia molded body or a zirconia pre-sintered body of the present invention is mainly a monoclinic system. In the present invention, "crystal system being mainly a monoclinic system" means that the fraction $f_m$ of the monoclinic system of zirconia calculated from formula (4) below is at least 50% of the total amount of all the crystal systems (monoclinic, tetragonal, and cubic) of zirconia. In a zirconia molded body or a zirconia pre-sintered body of the present invention, the fraction $f_m$ of the monoclinic system of zirconia is preferably at least 55%, more preferably at least 60%, even more preferably at least 70%, yet more preferably at least 75%, particularly preferably at least 80%, still more preferably at least 85%, most preferably at least 90% of the total amount of the monoclinic, tetragonal, and cubic crystal systems. The fraction $f_m$ of the monoclinic system can be calculated from formula (4) below, using peaks in an X-ray diffraction (XRD) pattern by CuKα radiation. The main crystal system in the zirconia molded body or zirconia pre-sintered body possibly contributes to raising shrinkage temperature and reducing firing time.

In a zirconia molded body or a zirconia pre-sintered body of the present invention, the peaks of tetragonal and cubic crystal systems may be essentially undetectable. That is, the fraction $f_m$ of the monoclinic system may be 100%.

[Math. 2]

$$f_m(\%) = \frac{I_m(111) + I_m(11-1)}{I_m(111) + I_m(11-1) + I_t(111) + I_c(111)} \times 100 \quad (4)$$

In formula (4), $I_m(111)$ and $I_m(11-1)$ represent the peak intensities of the (111) plane and (11-1) plane, respectively, of the monoclinic system of zirconia, $I_t(111)$ represents the peak intensity of the tetragonal (111) plane of zirconia, and $I_c(111)$ represents the peak intensity of the (111) plane of the cubic crystal system of zirconia.

In a zirconia molded body or a zirconia pre-sintered body of the present invention, $f_m/f_y$ is preferably 20 to 200, more preferably 25 to 100, even more preferably 30 to 60 when the yttria content is 3 mol % or more and less than 4.5 mol %. When the yttria content is 4.5 mol % or more and less than 5.8 mol %, $f_m/f_y$ is preferably 5 to 45, more preferably 10 to 40, even more preferably 15 to 35. When the yttria content is 5.8 mol % to 7.5 mol %, $f_m/f_y$ is preferably 2 to 40, more preferably 5 to 35, even more preferably 10 to 30.

A zirconia molded body or a zirconia pre-sintered body of the present invention may optionally comprise an additive. Examples of the additive include binders, colorants (including pigments and complex pigments), fluorescent agents, alumina ($Al_2O_3$), titanium oxide ($TiO_2$), and silica ($SiO_2$). The additive may be used alone, or two or more thereof may be used as a mixture.

Examples of the binders include polyvinyl alcohol, methyl cellulose, carboxymethyl cellulose, acrylic binders, wax binders (e.g., paraffin wax), polyvinyl butyral, polymethyl methacrylate, ethyl cellulose, polyethylene, polypropylene, an ethylene-vinyl acetate copolymer, polystyrene, atactic polypropylene, methacrylic resin, and stearic acid.

Examples of the pigments include oxides of at least one element selected from the group consisting of Ti, V, Cr, Mn, Fe, Co, Ni, Zn, Y, Zr, Sn, Sb, Bi, Ce, Pr, Sm, Eu, Gd, Tb, and Er (specifically, for example, $NiO$, $Cr_2O_3$), preferably oxides of at least one element selected from the group consisting of Ti, V, Cr, Mn, Fe, Co, Ni, Zn, Y, Zr, Sn, Sb, Bi, Ce, Pr, Sm, Eu, Gd, and Tb, more preferably oxides of at least one element selected from the group consisting of Ti, V, Cr, Mn, Fe, Co, Ni, Zn, Y, Zr, Sn, Sb, Bi, Ce, Sm, Eu, Gd, and Tb. A zirconia molded body or a zirconia pre-sintered body of the present invention may be a zirconia molded body or a zirconia pre-sintered body that does not contain erbium oxide ($Er_2O_3$). Examples of the complex pigments include composite oxides, for example, such as $(Zr,V)O_2$, $Fe(Fe,Cr)_2 O_4$, $(Ni,Co,Fe)(Fe,Cr)_2O_4ZrSiO_4$, and $(Co,Zn)Al_2O_4$. Examples of the fluorescent agents include $Y_2SiO_5:Ce$, $Y_2SiO_5:Tb$, $(Y,Gd,Eu)BO_3$, $Y_2O_3:Eu$, $YAG:Ce$, $ZnGa_2O_4:Zn$, and $BaMgAl_{10}O_{17}:Eu$.

The method used to produce a zirconia molded body in the present invention is not particularly limited. An example is a method that includes a step of pressing a mixed powder of zirconia and the stabilizer into a zirconia molded body under a pressure of 175 MPa or higher. By being pressed under this pressure, the mixed powder can form a zirconia molded body (and, in turn, a zirconia sintered body) having an increased bulk density, irrespective of the thickness. As used herein, "pressure of 175 MPa or higher" means the maximum pressure of press forming.

The method used to produce a zirconia pre-sintered body in the present invention is not particularly limited. In an example method, a zirconia molded body formed from a raw material powder containing zirconia particles and a stabilizer is fired (pre-sintered) at a temperature that does not sinter the zirconia particles. The zirconia molded body is as described above. An example of a method of producing a zirconia pre-sintered body of the present invention is described below. First, a raw material powder of zirconia molded body is produced. A powder of monoclinic zirconia is mixed with a stabilizer powder (for example, an yttria powder) to prepare a mixture having the desired stabilizer (for example, yttria) content. The mixture is added into water to make a slurry, and the slurry is pulverized and mixed wet with a ball mill until the particles reach the desired particle size. After pulverization, the slurry is dried to granulate, using a spray drier. The resultant powder is then fired to make a powder (primary powder) at a temperature (for example, 800 to 1,200° C.) that does not sinter the zirconia particles. A pigment may be added to the primary powder. The primary powder is then added into water to make a slurry, and the slurry is pulverized and mixed wet with a ball mill until the particles reach the desired particle size. After optionally adding an additive, such as a binder, to the pulverized slurry, the slurry is dried with a spray drier to obtain a mixed powder (secondary powder). The secondary powder is filled into a predetermined die, and, after leveling the top surface and installing an upper die, pressure is applied with a uniaxial pressing machine to form the secondary powder into a zirconia molded body. The pressure applied to press the mixed powder is preferably 175 MPa or higher. The zirconia molded body obtained may or may not be subjected to cold isostatic pressing (CIP).

The zirconia pre-sintered body may have a multilayer structure. When producing a multilayer zirconia pre-sintered body, the primary powder used in the method of production of a zirconia molded body may be divided into at least two (preferably four) separate portions to provide a multilayer structure in the zirconia molded body.

The zirconia molded body obtained in this fashion is pre-sintered to obtain a zirconia pre-sintered body. The pre-sintering temperature is, for example, preferably 800° C. or more, more preferably 900° C. or more, even more preferably 950° C. or more. For increased dimensional accuracy, the pre-sintering temperature is, for example, preferably 1,200° C. or less, more preferably 1,150° C. or less, even more preferably 1,100° C. or less. These pre-sintering temperatures are preferred because dissolution of the stabilizer does not seem to proceed in these temperature ranges.

The zirconia pre-sintered body used in the present invention may be a commercially available product. Examples of such commercially available products include Noritake KATANA® zirconia (Model: disc UTML, disc STML, disc ML, disc HT, disc LT; all manufactured by Kuraray Noritake Dental Inc.). In a method of production of a zirconia sintered body of the present invention, it is preferable that the commercially available zirconia pre-sintered body be used after being milled into a predetermined shape of a dental product.

In a method of production of a zirconia sintered body of the present invention, the rate of temperature increase in the temperature increasing step before shrinkage start temperature may be constant, or may be progressive with variable rates, provided that it is not detrimental to the effects of the present invention.

In view of providing a zirconia sintered body having superior lightness, translucency, and saturation, and enabling the composite oxides in the zirconia molded body or zirconia pre-sintered body to better develop color, the temperature increasing step in a method of production of a zirconia sintered body of the present invention may be followed by a step of further increasing temperature (second temperature-increasing step), after the temperature has reached the shrinkage end temperature. The second temperature-increasing step distinguishes itself from the temperature increasing step (first temperature-increasing step) in that the second temperature-increasing step is a temperature increasing step after zirconia has finished shrinking. The rate of temperature increase in the second temperature-increasing step is, for example, 10° C./min or more. In view of enabling further reduction of a processing time, the rate of temperature increase in the second temperature-increasing step is preferably 11° C./min or more, more preferably 12° C./min or more, even more preferably 13° C./min or more. In view of providing a zirconia sintered body having superior saturation and enabling the composite oxides in the zirconia molded body or zirconia pre-sintered body to better develop color, the rate of temperature increase in the second temperature-increasing step is, for example, 299° C./min or less, preferably 270° C./min or less, more preferably 250° C./min or less, even more preferably 200° C./min or less.

Retention Step

In view of facilitating development of translucency by grain growth, the heating step in a method of production of a zirconia sintered body of the present invention preferably includes a retention step of retaining the highest firing temperature of the temperature increasing step, following the temperature increasing step. Preferably, the highest firing temperature is retained for at most 30 minutes. In view of enabling further reduction of a processing time and providing a zirconia sintered body having excellent strength, the retention time is more preferably 1 to 30 minutes, even more preferably 10 to 20 minutes. The highest firing temperature is preferably 1,400 to 1,650° C. In view of providing a zirconia sintered body having superior lightness, translucency, and saturation, and enabling the composite oxides in the zirconia molded body or zirconia pre-sintered body to better develop color, the highest firing temperature is more preferably 1,450° C. or higher, even more preferably 1,500° C. or higher, particularly preferably 1,520° C. or higher. In view of enabling further reduction of a processing time and providing a zirconia sintered body having superior lightness, translucency, and saturation, and enabling the composite oxides in the zirconia molded body or zirconia pre-sintered body to better develop color, the highest firing temperature is more preferably 1,630° C. or less, even more preferably 1,620° C. or less, particularly preferably 1,610° C. or less.

In view of enabling further reduction of a processing time, the total firing time from the start of temperature increase in the temperature increasing step to the end of the retention period at the highest firing temperature in a method of production of a zirconia sintered body of the present invention is preferably at most 100 minutes, more preferably at most 80 minutes, even more preferably at most 50 minutes. The lower limit of the firing time is not limited, and the firing time is typically at least 10 minutes, provided that it is not detrimental to the effects of the present invention.

Cooling Step

Preferably, a method of production of a zirconia sintered body of the present invention comprises a step of cooling a zirconia sintered body after the zirconia sintered body is retained at the highest firing temperature for the predetermined time period. In the cooling step, the rate of temperature decrease is preferably 40° C./min or more, more preferably 45° C./min or more, even more preferably 50° C./min or more. The method of temperature decrease may be any of cooling by intake air from outside, water cooling, air cooling, gradual cooling, and letting the zirconia sintered body stand to cool, or a combination of these. The temperature reached at the end of the cooling step depends on factors such as the type and capabilities of the furnace, and may be 1,000° C., 900° C., or 800° C.

A zirconia sintered body obtained by a method of production of the present invention has a color difference $\Delta E^*ab$ of preferably 2.7 or less, more preferably 2.0 or less, even more preferably 1.6 or less, particularly preferably 0.8 or less because such a zirconia sintered body is suited as a dental product. Preferably, the color difference $\Delta E^*ab$ is measured against the chromaticity of a zirconia sintered body of when it is fired in a normal fashion (a total firing time: 6 to 12 hours). Chromaticity can be evaluated using known methods. The color difference $\Delta E^*ab$ is, for example, a color difference $\Delta E^*$ ($\Delta E^*ab$) determined from the following formula (5) for a sample zirconia sintered body ($L_1^*$, $a_1^*$, $b_1^*$) fired in a normal fashion, and a sample zirconia sintered body ($L_2^*$, $a_2^*$, $b_2^*$) subjected to short firing (a total firing time: 15 to 30 minutes) by measuring color with a dental colorimeter (a 7-band LED illuminant Crystaleye, manufactured by Olympus Corporation) using the lightness index L* and color coordinates a*, b* of the CIE 1976 L*a*b* color space.

$$\Delta E^* = \{(L_1^* - L_2^*)^2 + (a_1^* - a_2^*)^2 + (b_1^* - b_2^*)^2\}^{1/2} \qquad (5)$$

The difference between the lightness index L* of a zirconia sintered body obtained by a method of production of the present invention and the lightness index L* of a zirconia sintered body fired in a normal fashion (a total firing time: 6 to 12 hours) is preferably 2.0 or less, more preferably 1.5 or less, even more preferably 1.0 or less because a zirconia sintered body having such a difference is suited as a dental product. The L*, a*, and b* of a zirconia sintered body obtained by a method of production of the present invention can be selected and set according to where the zirconia sintered body is intended for, for example, such as the cervical region or the incisal edge.

The present invention encompasses embodiments combining the foregoing features, provided that such combinations made in various forms within the technical idea of the present invention can produce the effects of the present invention. In the present specification, the upper limits and lower limits of numeric ranges (for example, (rates of temperature increase, rates of temperature decrease, firing times, temperatures, rate ratios, and contents of components (for example, a stabilizer) can be combined appropriately.

EXAMPLES

The following describes the present invention in greater detail by way of Examples. It should be noted, however, that the present invention is in no way limited by the following Examples, and various changes may be made by a person with ordinary skill in the art within the technical idea of the present invention.

Method of Determination of Shrinkage Start Temperature and Shrinkage End Temperature In the Examples and Comparative Examples below, the shrinkage start temperature was determined by measuring the lowest firing temperature at which a prepared cuboidal sample block of unfired zirconia (1 cm×2 cm×1 cm) had a shrinkage rate of more than 0% when the sample block was fired with a furnace for 10 minutes at a firing temperature higher than the start temperature of the temperature increasing step. The shrinkage end temperature was determined by measuring the lowest temperature at which the difference between the shrinkage rate (%) at a firing temperature T (° C.) and the shrinkage rate (%) at a firing temperature T+50° C. was 0% when the temperature range of each zone of the shrinkage temperature region was 50° C.

Example 1

Figure 1B:
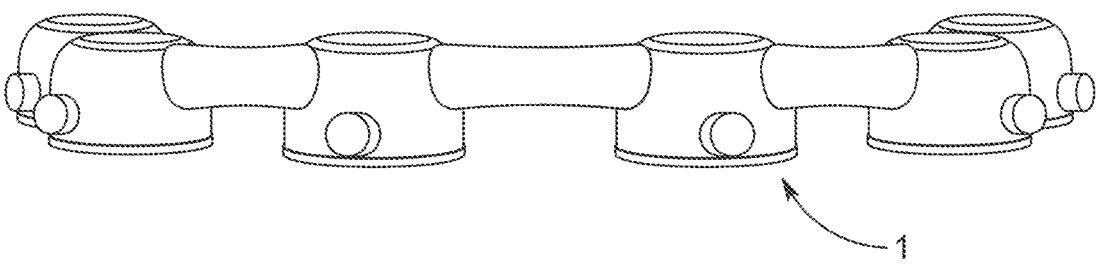

An HTML zirconia disc work (Noritake KATANA® zirconia, manufactured by Kuraray Noritake Dental Inc.) was milled into the shape shown in FIG. 1 ((a), plan view; (b), front view) to prepare a zirconia pre-sintered body sample, using a DWX52DC (manufactured by Roland D. G). The sample was fired with a furnace (F-2N, manufactured by SK Medical Electronics Co., Ltd.) under the firing schedule conditions shown in Table 1 to produce a zirconia sintered body (prosthesis).

TABLE 1

| Rate of temperature increase (° C./min) | Zone (° C.) | Retention time (min) |
|---|---|---|
| 50 | 0 to 1000 | 0 |
| 42 | 1000 to 1050 | 0 |
| 13 | 1050 to 1100 | 0 |
| 7 | 1100 to 1150 | 0 |
| 6 | 1150 to 1200 | 0 |

TABLE 1-continued

| Rate of temperature increase (° C./min) | Zone (° C.) | Retention time (min) |
|---|---|---|
| 5 | 1200 to 1250 | 0 |
| 21 | 1250 to 1300 | 0 |
| 16 | 1300 to 1350 | 0 |
| 50 | 1350 to 1400 | 0 |
| 50 | 1400 to 1450 | 0 |
| 50 | 1450 to 1500 | 0 |
| 50 | 1500 to 1515 | 0 |
| 0 | 1515 | 30 |
| −45 | 1515 to 800 | 0 |

In Example 1, the shrinkage start temperature and shrinkage end temperature were determined to be 1,000° C. and 1,400° C., respectively, according to the above method. The rate of temperature increase in each zone of the temperature region from the shrinkage start temperature to the shrinkage end temperature was set according to the method including the Steps 1 to 5 described above. In Step 1, the temperature region was divided into 50° C. temperature ranges, and the shrinkage rates in response to firing at the temperatures at the boundaries of each zone (temperature range) were measured. Table 2 shows the shrinkage rate difference of each zone calculated in Step 2, and the coefficient of shrinkage of each zone calculated in Step 3. In Step 4, the acceptable rate of temperature increase in each zone was calculated with the maximum rate of temperature increase of furnace set at 50° C./min. In Step 5, the rate of temperature increase was set to be 1.0 times the acceptable rate of temperature increase in each zone.

TABLE 2

| Zone (° C.) | Zonal shrinkage rate difference (%) | Zonal coefficient of shrinkage |
|---|---|---|
| 1000 to 1050 | 0.6 | 1.2 |
| 1050 to 1100 | 2.0 | 4.0 |
| 1100 to 1150 | 3.6 | 7.2 |
| 1150 to 1200 | 4.2 | 8.4 |
| 1200 to 1250 | 5.1 | 10.2 |
| 1250 to 1300 | 1.2 | 2.4 |
| 1300 to 1350 | 1.6 | 3.2 |
| 1350 to 1400 | 0.5 | 1.0 |

Example 2

A zirconia sintered body (prosthesis) was produced in the same manner as in Example 1, except that a Noritake KATANA® zirconia HT (a zirconia pre-sintered body manufactured by Kuraray Noritake Dental Inc.) was used as a zirconia disc work, and the firing schedule was changed as shown in Table 3. Table 4 shows the shrinkage rate difference of each zone calculated in Step 2, and the coefficient of shrinkage of each zone calculated in Step 3. In Step 5, the rate of temperature increase was set to be 1.0 times the acceptable rate of temperature increase in each zone.

TABLE 3

| Rate of temperature increase (° C./min) | Zone (° C.) | Retention time (min) |
|---|---|---|
| 50 | 0 to 1000 | 0 |
| 50 | 1000 to 1050 | 0 |
| 11 | 1050 to 1100 | 0 |
| 7 | 1100 to 1150 | 0 |
| 6 | 1150 to 1200 | 0 |

TABLE 3-continued

| Rate of temperature increase (° C./min) | Zone (° C.) | Retention time (min) |
|---|---|---|
| 5 | 1200 to 1250 | 0 |
| 21 | 1250 to 1300 | 0 |
| 16 | 1300 to 1350 | 0 |
| 50 | 1350 to 1400 | 0 |
| 50 | 1400 to 1450 | 0 |
| 50 | 1450 to 1500 | 0 |
| 50 | 1500 to 1515 | 0 |
| 0 | 1515 | 30 |
| −45 | 1515 to 800 | 0 |

TABLE 4

| Zone (° C.) | Zonal shrinkage rate difference (%) | Zonal coefficient of shrinkage |
|---|---|---|
| 1000 to 1050 | 0.5 | 1.0 |
| 1050 to 1100 | 2.2 | 4.4 |
| 1100 to 1150 | 3.4 | 6.8 |
| 1150 to 1200 | 4.4 | 8.8 |
| 1200 to 1250 | 4.9 | 9.8 |
| 1250 to 1300 | 1.2 | 2.4 |
| 1300 to 1350 | 1.6 | 3.2 |
| 1350 to 1400 | 0.5 | 1.0 |

Example 3

A zirconia sintered body (prosthesis) was produced in the same manner as in Example 1, except that a Noritake KATANA® zirconia STML (a zirconia pre-sintered body manufactured by Kuraray Noritake Dental Inc.) was used as a zirconia disc work, and the firing schedule was changed as shown in Table 5. Table 6 shows the shrinkage rate of each zone calculated in Step 2, and the coefficient of shrinkage of each zone calculated in Step 3. In Step 5, the rate of temperature increase was set to be 1.0 times the acceptable rate of temperature increase in each zone.

TABLE 5

| Rate of temperature increase (° C./min) | Zone (° C.) | Retention time (min) |
|---|---|---|
| 50 | 0 to 1000 | 0 |
| 50 | 1000 to 1050 | 0 |
| 14 | 1050 to 1100 | 0 |
| 17 | 1100 to 1150 | 0 |
| 6 | 1150 to 1200 | 0 |
| 7 | 1200 to 1250 | 0 |
| 5 | 1250 to 1300 | 0 |
| 11 | 1300 to 1350 | 0 |
| 50 | 1350 to 1400 | 0 |
| 50 | 1400 to 1450 | 0 |
| 50 | 1450 to 1500 | 0 |
| 50 | 1500 to 1515 | 0 |
| 0 | 1515 | 30 |
| −45 | 1515 to 800 | 0 |

TABLE 6

| Zone (° C.) | Zonal shrinkage rate difference (%) | Zonal coefficient of shrinkage |
|---|---|---|
| 1000 to 1050 | 0.4 | 1.0 |
| 1050 to 1100 | 1.8 | 3.6 |
| 1100 to 1150 | 1.5 | 3.0 |
| 1150 to 1200 | 4.0 | 8.0 |
| 1200 to 1250 | 3.8 | 7.6 |

TABLE 6-continued

| Zone (° C.) | Zonal shrinkage rate difference (%) | Zonal coefficient of shrinkage |
|---|---|---|
| 1250 to 1300 | 5.2 | 10.4 |
| 1300 to 1350 | 2.2 | 4.4 |
| 1350 to 1400 | 0.5 | 1.0 |

Comparative Example 1

A zirconia sintered body (prosthesis) was produced in the same manner as in Example 1, except that the firing schedule was changed as shown in Table 7.

TABLE 7

| Rate of temperature increase (° C./min) | Zone (° C.) | Retention time (min) |
|---|---|---|
| 35 | 0 to 1515 | 0 |
| 0 | 1515 | 30 |
| −45 | 1515 to 800 | 0 |

Comparative Example 2

A zirconia sintered body (prosthesis) was produced in the same manner as in Example 2, except that the firing schedule was changed as shown in Table 7.

Comparative Example 3

A zirconia sintered body (prosthesis) was produced in the same manner as in Example 3, except that the firing schedule was changed as shown in Table 8.

TABLE 8

| Rate of temperature increase (° C./min) | Temperature (° C.) | Retention time (min) |
|---|---|---|
| 35 | 0 to 1560 | 0 |
| 0 | 1560 | 30 |
| −45 | 1560 to 800 | 0 |

Model Conformity

Figure 2A:
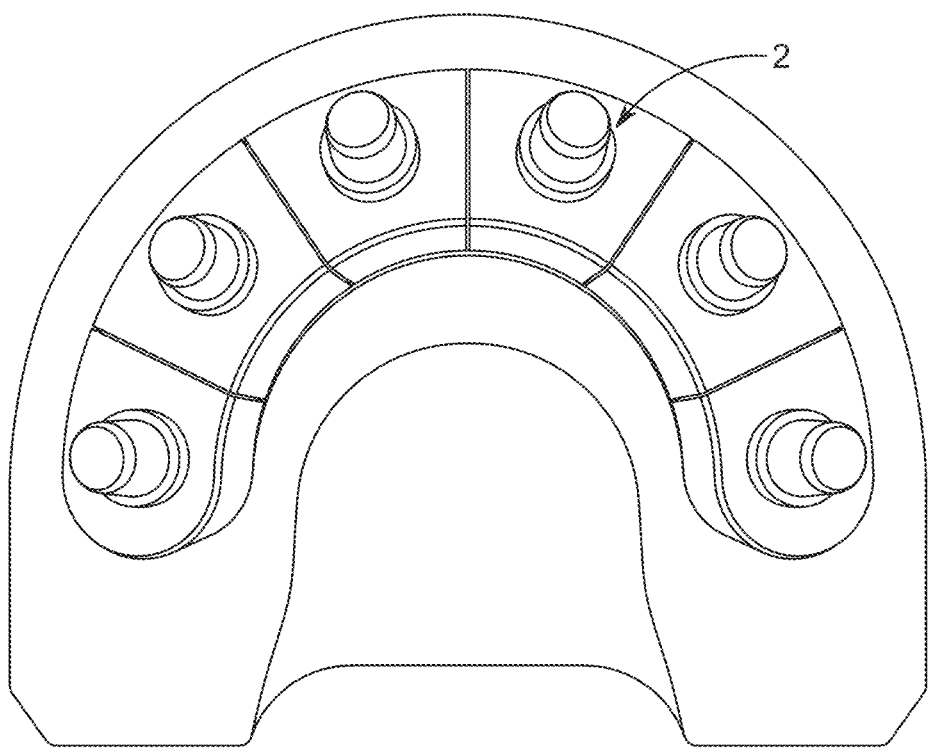
FIG. 2 is a diagram showing a model used for evaluation of model conformity of the prostheses produced in Examples 1 to 3 and Comparative Examples 1 to 3.
Figure 2B:
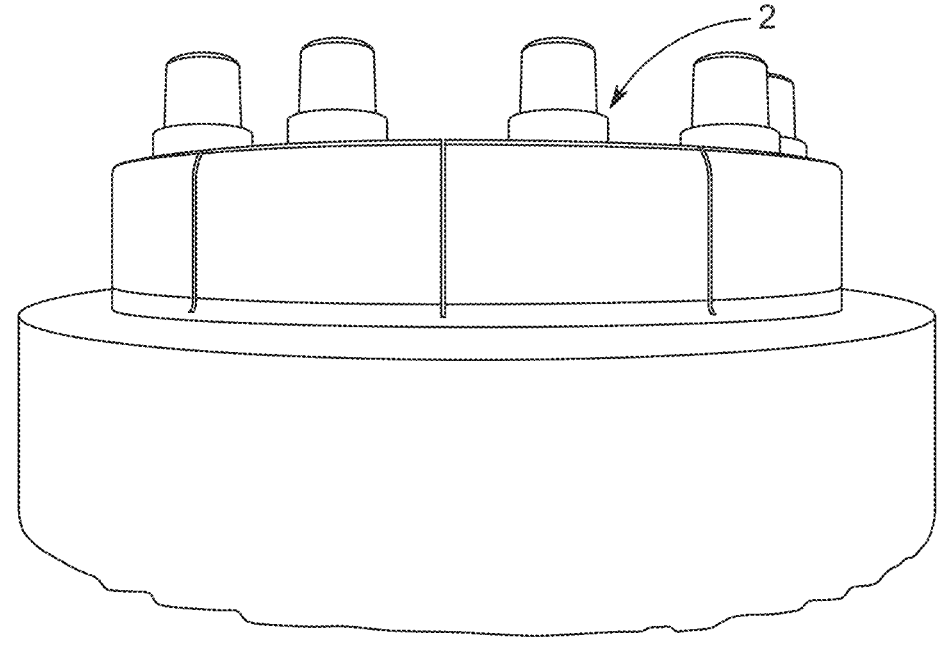

A model was fabricated to simulate a long-span bridge, as shown in FIG. 2 ((a), plan view, (b), front view). The prosthesis (n=1) of the shape shown in FIG. 1 fabricated in each Example and Comparative Example was assessed for its conformity to the model. Conformity was "Good" when there was no visually observable distance (gap) at the marginal portions when the prosthesis of the shape shown in FIG. 1 was installed in the model shown in FIG. 2, and "Poor" when a distance was confirmed at the marginal portions. The distance between the marginal portion 1 of the prosthesis and the marginal portion 2 of the model was measured (the distance between the marginal portions when the prosthesis of the shape shown in FIG. 1 was installed in the model shown in FIG. 2), and a mean value of values from six measurement points was calculated. The results of evaluation are presented in FIG. 3.

Figure 3:
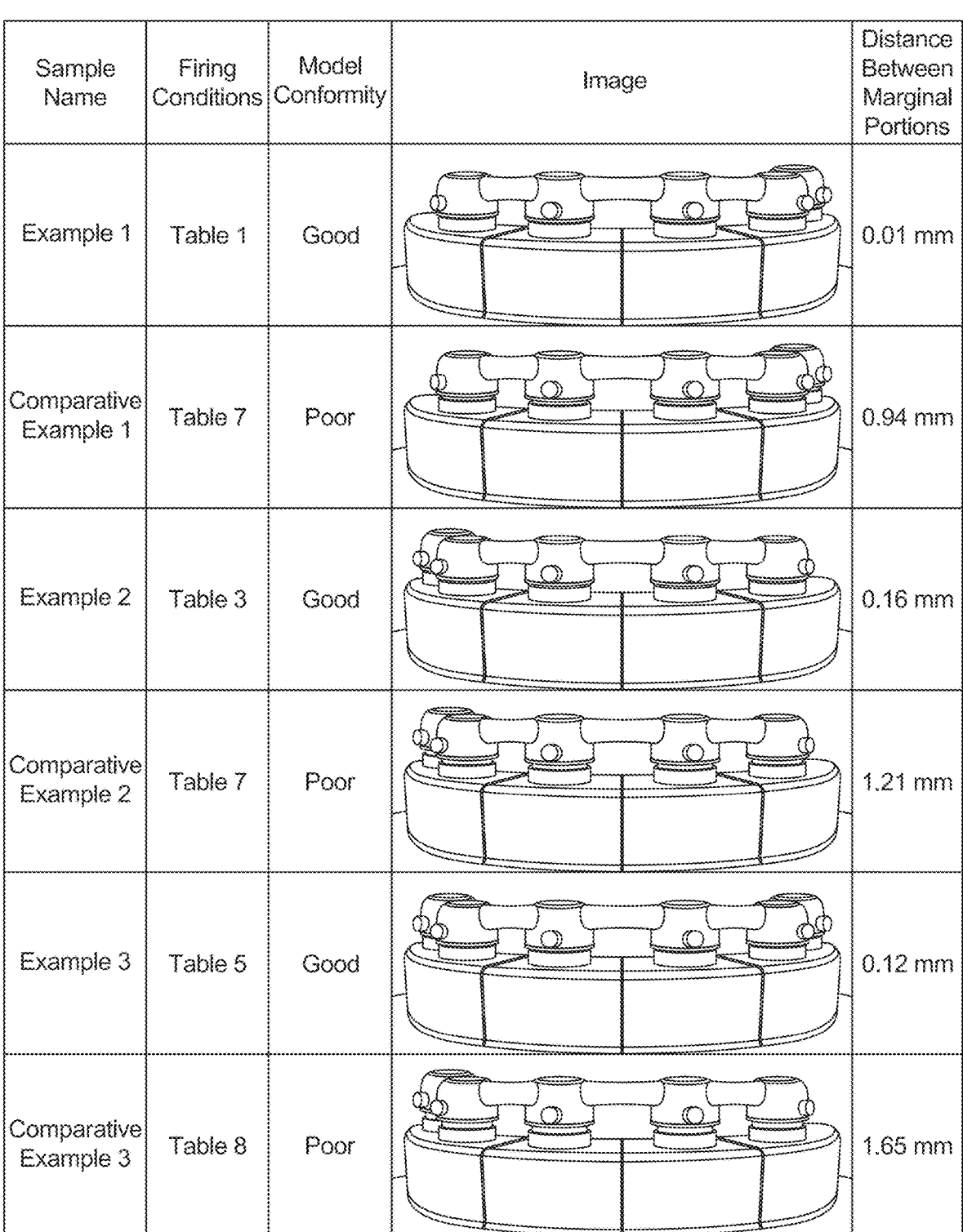
FIG. 3 is a diagram showing firing schedules of the prostheses produced in Examples 1 to 3 and Comparative Examples 1 to 3, along with evaluation results.

The zirconia sintered bodies of Examples 1 to 3 all conformed to the model, as shown in the image shown in FIG. 3, and had a very small distance of 0.01 to 0.16 mm between the marginal portions, confirming that deformation during firing was reduced. The zirconia sintered bodies of Comparative Examples 1 to 3 all had a 0.94 to 1.65 mm gap between the marginal portion 1 of the prosthesis and the marginal portion 2 of the model, and did not conform to the model, confirming that deformation during firing was not reduced. From these results, it was confirmed that the zirconia sintered bodies obtained by using a method of production of the present invention are firable in a short time period, and can have reduced deformation even when it is a large-sized prosthesis, without limiting the composition. The results showed that the zirconia sintered bodies are suited as dental products (for example, dental prostheses).

INDUSTRIAL APPLICABILITY

A method of production of a zirconia sintered body of the present invention enables sintering of a zirconia molded body or a zirconia pre-sintered body in a short time period, and the zirconia sintered body obtained can be fired in a short time period to reduce deformation even in large-sized prostheses, without limiting the composition. This makes the method useful for the production of dental products (for example, dental prostheses). The method is particularly useful for the production of a large dental prosthesis with three or more bridge units, such as a long-span bridge.

REFERENCE SIGNS LIST

1 Marginal portion of prosthesis
2 Marginal portion of model
The invention claimed is:
1. A method for producing a zirconia sintered body, comprising:
  heating a zirconia molded body or a zirconia pre-sintered body, where the heating comprises a temperature increasing step, and a rate of temperature increase in a temperature region from a temperature at which the zirconia molded body or a zirconia pre-sintered body starts to shrink to a temperature at which the zirconia molded body or a zirconia pre-sintered body finishes shrinking in the temperature increasing step is adjusted to enable the zirconia molded body or the zirconia pre-sintered body to shrink at a substantially constant rate across the temperature region during the temperature increase in each of a plurality of zones of when the temperature region is evenly divided into the plurality of zones of specific temperature ranges,
  wherein the rate of temperature increase in each zone is set to 0.1 to 1.0 times an acceptable rate of temperature increase in each zone calculated from the formula (1) below, and a ratio of the rate of temperature increase in each zone to the acceptable rate of temperature increase in each zone is substantially the same, $$\text{(Acceptable rate of temperature increase in each zone)}=\text{(maximum rate of temperature increase of furnace)/(coefficient of shrinkage of each zone)} \qquad (1),$$

wherein the coefficient of shrinkage of each zone in formula (1) is represented by the following formula (2), $$\text{(Coefficient of shrinkage of each zone)}=\text{(shrinkage rate difference of each zone)/(temperature range/100)} \qquad (2),$$

wherein the formula (1) is solved by assuming that the coefficient of shrinkage of each zone is 1 when the coefficient of shrinkage of each zone calculated using formula (2) is less than 1,
  wherein the shrinkage rate difference of each zone is the difference between the shrinkage rate at the start temperature and end temperature of each zone.
2. The method according to claim 1, wherein the specific temperature range of each zone is 50° C.
3. The method according to claim 1, wherein the temperature region ranges from 1,050 to 1,400° C.
4. The method according to claim 1, which has a total firing time of at most 120 minutes from a start of temperature increase in the temperature increasing step to an end of a retention period at the highest firing temperature of the temperature increasing step.
5. The method according to claim 1, wherein the heating further includes a retention step of retaining the highest firing temperature of the temperature increasing step, following the temperature increasing step.
6. The method according to claim 1, wherein the zirconia sintered body is suitable for dental use.

* * * * *